United States Patent [19]

Mimoun et al.

[11] Patent Number: 5,554,786
[45] Date of Patent: Sep. 10, 1996

[54] PROCESS FOR THE PREPARATION OF CARBOXYLIC ESTERS DEFINED FROM ALLYLIC ALCOHOLS

[75] Inventors: Hubert Mimoun, Challex, France; Chengguo Jia, Ames, Iowa

[73] Assignee: Firmenich S.A., Geneva, Switzerland

[21] Appl. No.: 436,069

[22] Filed: May 5, 1995

[30] Foreign Application Priority Data

Jun. 1, 1994 [CH] Switzerland ............... 1704/94

[51] Int. Cl.$^6$ ................................. C07C 67/05
[52] U.S. Cl. ................................................ 560/243
[58] Field of Search ............................. 560/243

[56] References Cited

FOREIGN PATENT DOCUMENTS 1191362  4/1965  Germany.

OTHER PUBLICATIONS

Hansson et al.; "Preparation of Allylic Acetates from Simple Alkenes by Palladium (II)—Catalyzed Acetoxylation", J. Org. Chem. 1990, 55, 975–984.

Greenberg et al.; "Iron Phthalocyanine as a Catalyst for the Aerobic Oxidation of Hydroquinone to 1,4–Benzoquinone. A Simple Test for Catalytic 'Oxidase' Activity", Acta Chemica Scandinavica 47 (1993) 506–508.

Larsson et. al.; "A Catalytic System for Allylic Acetoxylation Consisting of Palladium (II) and Nitrate and Using Oxygen as Final Oxidant", Tetrahedron Letters, vol. 34, No. 15 pp. 2523–2526, 1993.

Bäckvall et al.; "Multistep Electron Transfer in Palladium–Catalyzed Aerobic Oxidations via a Metal Macrocyle–Quinone System"; J. Am. Chem. Soc. 1990, 112, 5160–5166.

Grennberg et al.; "Use of Sulfoxides as Cocatalysts in the Palladium–Quinone–Catalyzed 1, 4 Diacetoxylation of 1,3–Dienes. An Example of Ligand–Accelerated Catalysis"; J. Org. Chem. 1991, 56, 5808–5811.

*Primary Examiner*—Michael L. Shippen
*Attorney, Agent, or Firm*—Pennie & Edmonds

[57] ABSTRACT

A process which comprises reacting an aliphatic or cycloaliphatic olefin, having 4 to 16 carbon atoms in its main chain and a non-terminal double bond, with a carboxylic acid, in the presence of hydrogen peroxide and a catalyst consisting of a palladium salt or complex.

7 Claims, No Drawings

PROCESS FOR THE PREPARATION OF CARBOXYLIC ESTERS DEFINED FROM ALLYLIC ALCOHOLS

BRIEF SUMMARY OF THE INVENTION

The invention relates to a process for the preparation of carboxylic esters derived from allylic alcohols via allylic acyloxylation of olefins, wherein an aliphatic or cycloaliphatic olefin, having 4 to 16 carbon atoms in its main chain and a non-terminal double bond, is treated with a carboxylic acid in the presence of hydrogen peroxide and a catalyst consisting of a palladium salt or complex.

BACKGROUND OF THE INVENTION

A large number of carboxylic esters derived from allylic alcohols have been mentioned in the literature as useful intermediates for the preparation of compounds which are of interest in the perfume and flavor industry, as well as for a variety of specialities in the pharmaceutical industry.

Now, such esters have been obtained in the past, with a mixed degree of success, by oxidation of the corresponding olefins.

Various methods have been devised to this end. However, none of these methods is entirely satisfactory.

Thus, when the oxidation of said olefins is carried out for example by air autoxidation, it leads to poorly selective reactions, the intermediate primary hydroperoxide decomposing to provide a mixture of enols and enones. Furthermore, this type of reaction requires large volume reactors and recycling of the starting olefin.

Another method, which consists in the allylic oxidation of the olefins by the action of selenium dioxide, is likewise poorly selective and requires the use of considerable amounts of $SeO_2$, a toxic and environmentally harmful reagent.

Yet another known method of allylic oxidation resorts to the use of palladium catalysts. For example, allyl acetate, a useful intermediate for the preparation of allyl alcohol, can be obtained by acetoxylation of propene in the presence of palladium. The same applies to the industrial production of 1,4-diacetoxy-but-2-ene.

In this type of reaction, one generally uses a palladium catalyst, preferably on a solid carrier or support such as for example silica or alumina doped with alkaline acetates and/or gold, iron or bismuth (allyl acetate) salts, or with tellurium oxide (1,4-diacetoxy-butene) [see H. Mimoun in "Comprehensive Coordination Chemistry", Ed. Wilkinson, vol. 6, p. 318 (1983) and references therein]. This type of process has not turned out to be very satisfactory either, because, in practice, the conversion does not proceed to completion.

The situation is even more problematic when using superior olefins.

All of the above-described systems use molecular oxygen as oxidizing agent. When employing as catalyst a palladium salt, i.e. in the form of an acetate, the latter is used in relatively high amounts, generally above 2% by weight with regard to the starting product. The reaction is also carried out in the presence of various palladium re-oxidizing agents, such as for example the alkaline nitrates [Tetrah. Lett. 1993, 34, 2523], or benzoquinone [J. Am. Chem. Soc. 1990, 112, 5160; Acta Chem. Scand. 1993, 47, 506; J. Org. Chem. 1991, 56, 5808]together with manganese dioxide, in stoichiometric concentration [J. Org. Chem 1990, 55, 975], or yet of co-catalysts which make it possible to re-oxidize the formed hydroquinone into benzoquinone, by means of the molecular oxygen.

As we have seen, these prior art methods use complex, costly and unprofitable redox systems, in which the recovery and recycling of the precious metal poses difficult technical problems.

We have now discovered that it is possible to carry out reactions of allylic acyloxylation of olefins by reacting the latter with hydrogen peroxide, in the presence of a catalyst consisting of a palladium salt or complex and in the presence of a carboxylic acid.

DETAILED DESCRIPTION OF THE INVENTION

The object of the present invention is therefore to provide a process for the preparation of carboxylic esters derived from allylic alcohols via allylic acyloxylation of olefins, wherein an aliphatic or cycloaliphatic olefin, having 4 to 16 carbon atoms in its main chain and possessing a nonterminal double bond, is treated with a carboxylic acid in the presence of hydrogen peroxide and of a catalyst consisting of a palladium salt or complex.

The reaction which characterizes the process of the invention can be illustrated by way of the following reaction scheme.

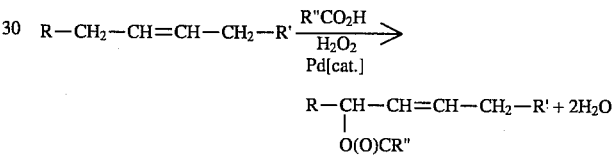

wherein R, R' and R" represent each a hydrogen atom or an alkyl radical.

When applied to cycloaliphatic olefins, this same type of reaction makes it possible to obtain, in an analogous manner, the corresponding allylic esters. For example, by allylic acyloxylation of cyclopentene there is obtained 3-acyloxy-cyclopentene.

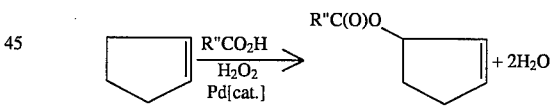

As the starting olefin, a variety of mono- or polyunsaturated olefins, having a linear or branched chain, whether substituted or unsubstituted, can be used. Amongst these, there can be cited cis- or trans- but-2-ene, 2-methyl-but-2-ene, pent-2-ene, pent-3-ene, oct-2-ene, oct-3-ene, oct-4-ene, hexa-1,5-diene, 2,4,4-trimethyl-pent-2-ene, 1-phenyl-propene, isosafrole or iso-methyleugenol.

Examples of cycloolefins that can be used include cyclopentene, cyclohexene, cycloheptene, cis- or trans-cyclooctene, cis- or trans-cyclododecene, cyclohexadecene, cyclopentadiene, cyclohexa-1,3-diene, cyclohexa-1,4-diene, dicyclopentadiene, cycloocta-1,5-diene, α-pinene, β-pinene, δ-3-carene, 4-vinyl-cyclohexene or dimethyl-octa-1,5-diene. It has been observed that the reaction proceeds in the most selective way on a substrate such as cyclopentene, cyclohexene or cycloheptene.

As the carboxylic acid, a great variety of carboxylic acids can be employed, whether of aromatic or of saturated or unsaturated, substituted or unsubstituted, aliphatic chain.

Examples include acetic acid, propionic acid, butyric acid, isobutyric acid, benzoic acid, 2-ethyl-hexanoic acid, acrylic acid, crotonic acid and methacrylic acid. Acetic acid is preferably used.

The acid reagent is used at the rate of at least one molar equivalent, with regard to the starting olefin.

As indicated above, the reaction is carried out in the presence of hydrogen peroxide. To this end, the use of an aqueous solution of $H_2O_2$, the concentrations of which can vary in a wide range of values, is quite convenient. Preferably, $H_2O_2$ is used in concentrations of the order of 30 to 70% by weight. One also uses at least one molar equivalent of this reagent, relative to the starting olefin, thus entailing almost complete conversion of the latter.

According to a preferred embodiment of the process of the invention, $H_2O_2$ is added to the reaction mixture containing the olefin, the catalyst and the carboxylic acid, the nature of these reagents being selected so as to avoid the decomposition of the catalyst and the resulting precipitation of metallic palladium.

As indicated above, the reaction takes place in the presence of a catalyst consisting of a palladium salt or complex. We have observed that such salts were preferably formed of palladium acetate or trifluoroacetate, palladium chloride or bromide, or of $Na_2PdCl_4$. As a palladium complex, one can advantageously use palladium tetrakis-(triphenylphosphine). A palladium salt or complex deposited on a support such as charcoal, alumina or silica can also be used.

For economic and practical reasons, palladium acetate will be preferentially used.

While the use of a co-catalyst is not indispensable to good reaction evolution, it became apparent that the stability of the catalyst could be improved by adding a quinone to the reaction mixture. Furthermore, the selectivity of said reaction was also enhanced, in as much as the allylic acyloxylation was favored over the epoxidation of the olefins, an undesired side reaction.

As the quinone, benzoquinone or naphthoquinone is used, in a molar concentration comprised between 1 and 10%, relative to the starting olefin.

We also observed that another advantageous measure consisted in adding to the reaction medium, in addition to the catalyst and, as the case may be, the quinone, an organic or inorganic solid support such as charcoal, alumina or silica. These supports not only promote the selectivity of the reaction, but they also favor the recovery of the catalyst and, consequently, its recycling.

The invention is illustrated by way of the following examples, wherein the temperatures are indicated in degrees Celsius and the abbreviations have the usual meaning in the art.

EXAMPLE 1

Acetoxylation of cyclohexene

A 500 ml three-neck flask was charged with 15 g of cyclohexene (0.18 moles), 150 g of acetic acid and 80 mg of palladium acetate (0.36 mmoles). The temperature was taken to 50°, and then 10.6 g (0.22 moles) of 70% by weight hydrogen peroxide were introduced in 8 h. The reaction was continued for 2 more hours, while keeping the temperature at 50°. The acetic acid was then distilled (35°, 20×10²Pa). The residue was distilled under vacuum (64°–68°, 15×10²Pa) to provide cyclohex-2-en-1-yl acetate, 90% pure (13 g, yield 50%). cyclohex-2-en-1-yl-acetate NMR($^1$H, 200MHz, CDCl$_3$): 5.90(m, 1H); 5.65(m, 1H); 5.21(broad m, 1H); 2.02(s, 3H); 1.5–2.1(m, 6H)δppm NMR($^{13}$C): 170.45; 132.29; 125.53; 67.84; 28.06; 24.82; 21.05; 18.80 δppm MS: m/e 140(M$^+$)

EXAMPLE 2

Acetoxylation of cyclohexene

The method described in Example 1 is followed but adding 0.77 g of benzoquinone (7 mmoles) and dividing by 4 the amount of palladium acetate (20 mg, 0.09 mmoles). The temperature is taken to 50°, then 10.6 g (0.22 moles) of 70% by weight hydrogen peroxide are introduced in 8 h, and the reaction is allowed to proceed for a further 2 h while maintaining the temperature at 50°. The acetic acid is then distilled (35°, 20×10² Pa). The residue is distilled under vacuum (64°–68°, 15×10² Pa) to provide 98% pure cyclohex-2-en-1-yl acetate (18 g, yield 70%). This example shows that, when operating in the presence of benzoquinone, both the yield and the selectivity of the reaction are increased, while using distinctly smaller amounts of palladium catalyst.

EXAMPLE 3

Acétoxylation du cyclopentène A 500 ml three-neck flask is charged with 15 g of cyclopentene (0.22 moles), 150 g of acetic acid, 0.77 g of benzoquinone (7 mmoles) and 80 mg of palladium acetate (0.35 mmoles). The temperature is taken to 50°, then 12 g (0.25 moles) of 70% by weight hydrogen peroxide are introduced in 8 h, and the reaction is allowed to proceed for a further 2 h while maintaining the temperature at 50°. The acetic acid is then distilled (35°, 20×10² Pa). The residue is distilled under vacuum (56°–60°, 15×10² Pa) to provide cyclopent-2-en-1-yl acetate (13 g, yield 60%). cyclopent-2-en-1-yl acetate NMR($^1$H, 200MHz, CDCl$_3$): 6.00(m, 1H); 5.65(m, 1H); 5.58(m, 1H); 1.90(s, 3H); 1.7–2.5(m, 4H)δppm NMR($^{13}$C): 170.85; 137.36; 129.18; 80.33; 30.94; 29.64; 21.14 δppm MS: m/e 126(M$^+$)

EXAMPLE 4

Acetoxylation of cycloheptene A 500 ml three-neck flask is charged with 15 g of cycloheptene (0.15 moles), 150 g of acetic acid, 0.77 g of benzoquinone (7 mmoles), 1 g of charcoal and 80 mg of palladium acetate (0.35 mmoles). The temperature is taken to 50°, then 8 g (0.17 moles) of 70% by weight hydrogen peroxide are introduced in 8 h, and the reaction is allowed to proceed for a further 2 h while maintaining the temperature at 50°. The acetic acid is then distilled (35°, 20×10² Pa). The residue is distilled under vacuum (75°–80°, 15×10² Pa) to provide cyclopent-2-en-1-yl acetate (14 g, yield 62%). cyclopent-2-en-1-yl acetate NMR($^1$H, 200MHz, CDCl$_3$): 5.74(m, 1H); 5.61(m, 1H); 5.34(m, 1H); 2.00(s, 3H); 1.20–2.20(m, 8H)δppm NMR($^{13}$C): 170.29; 133.60; 131.43; 74.29; 32.75; 28.38; 26.53; 26.48; 21.20 δppm MS: m/e 154(M$^+$)

EXAMPLE 5

Acetoxylation of 1-methylcyclohexene A 500 ml three-neck flask is charged with 15 g of 1-methylcyclohexene (0.15 moles), 150 g of acetic acid, 0.77 g of benzoquinone (7 mmoles), 1 g of active charcoal and 80 mg of palladium acetate (0.35 mmoles). The temperature is taken to 50°, then 8 g (0.17 moles) of 70% by weight hydrogen peroxide are introduced in 8 h, and the reaction is allowed to proceed for a further 2 h while maintaining the temperature at 50°. The acetic acid is then distilled (35°, 20×10² Pa). The residue is distilled under vacuum (75°–80°, 15×10² Pa) to provide 2-methyl-cyclohex-2-en-1-yl acetate (11 g, yield 50%).
2-methyl-cyclohex-2-en-1-yl acetate NMR(¹H, 200MHz, CDCl₃): 5.72(m, 1H); 5.2(t, 1H); 2.04(s, 3H); 1.66(d, J=1.6Hz, 3H); 1.70–2.12(m, 6H)δppm NMR(¹³C): 170.90; 131.70; 127.8; 70.66; 28.85; 25.10; 21.22; 20.09; 18.32 δppm MS: m/e 154(M⁺)

EXAMPLE 6

Acetoxylation of trans-cyclododecene

The method described in the preceding example is followed using 24 g of trans-cyclododecene (0.14 moles), 150 g of acetic acid, 0.77 g of benzoquinone (7 mmoles), 1 g of charcoal, 80 mg of palladium acetate (0.35 mmoles) and introducing 5.6 g of 70% by weight $H_2O_2$ in 10 h. After evaporating the acetic acid, 20 g of cyclododec-2-en-1-yl acetate are recovered by distillation under strong vacuum (molar yield 63%). cyclododec-2-en-1-yl acetate NMR(¹H): 5.75(m, 1H); 5.35(m, 1H); 5.14(m, 3H); 2.03(s, 3H); 1.0–2.2(m, 18H)δppm NMR(¹³C): 170.28; 135.13; 129.17; 70.01; 32.07; 31.64; 25.82; 25.60; 24.93; 24.88; 24.52; 24.32; 23.69; 21.45 δppm

EXAMPLE 7

Acetoxylation of l'hexa-1,5-diene

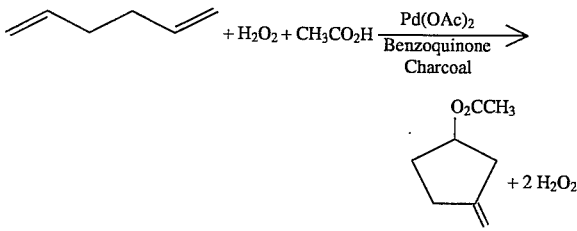

A 500 ml three-neck flask is charged with 15 g of hexa-1, 5-diene (0.18 moles), 150 g of acetic acid, 0.77 g of benzoquinone (7 mmoles), 1 g of charcoal and 80 mg of palladium acetate (0.35 mmoles). The temperature is taken to 50°, then 7 g (0.14 moles) of 70% by weight hydrogen peroxide are introduced in 8 h, and the reaction is allowed to proceed for a further 2 h while maintaining the temperature at 50°. The acetic acid is then distilled (35°, 20×10² Pa). The residue is distilled under vacuum to provide 1-acetoxy-3-methylene-cyclopentane in 65% molar yield. 1-acetoxy-3-methylene-cyclopentane NMR(¹H): 5.2(m, 1H); 4.91(m, 2H); 2.03(s, 3H); 2.40(m, 4H); 1.90(m, 2H)δppm NMR(¹³C): 170.78; 148.83; 106.81; 75.99; 39.27; 32.17; 30.05; 21.21 δppm

What we claim is:

1. A process for the preparation of carboxylic esters derived from allylic alcohols via allylic acyloxylation of olefins, wherein an aliphatic or cycloaliphatic olefin, having 4 to 16 carbon atoms in its main chain and possessing a non-terminal double bond, is treated with a carboxylic acid in the presence of hydrogen peroxide and of a catalyst consisting of a palladium salt or complex.

2. A process according to claim 1, wherein the reaction is carried out in the presence of a quinone.

3. A process according to claim 1, wherein the reaction is carried out in the presence of charcoal or silica.

4. A process according to claim 1, wherein the carboxylic acid is used at a rate of at least one molar equivalent, with regard to the starting olefin.

5. A process according to claim 1, wherein the hydrogen peroxide is used at a rate of at least one molar equivalent, with regard to the starting olefin.

6. A process according to claim 1, wherein the carboxylic acid is selected from the group consisting of acetic acid, propionic acid, butyric acid, benzoic acid and acrylic acid.

7. A process according to claim 1, wherein the catalyst is palladium acetate, palladium trifluoroacetate, palladium chloride or palladium bromide, or palladium tetrakis-(triphenylphosphine).

* * * * *

UNITED STATES PATENT AND TRADEMARK OFFICE
CERTIFICATE OF CORRECTION

PATENT NO. : 5,554,786

DATED : September 10, 1996

INVENTOR(S) : Hubert Mimoun and Chengguo Jia

It is certified that error appears in the above-identified patent and that said Letters Patent is hereby corrected as shown below:

Column 4, line 24: "Acétoxylation due cyclopentè" should read: Acetoxylation of cyclopentene; and after this phrase, please skip a line to separate from the text.

Column 4, line 41: after "Acetoxylation of cycloheptene", please skip a line to separate from the text.

Column 4, line 50 and 51: in each instance of "cyclopent-2-", should read cyclohept-2-.

Column 4, line 59: after "Acetoxylation of 1-methylcyclohexene", please skip a line to separate from the text.

Column 5, line 27: delete "l'" before "hexa-1,5-diene".

Signed and Sealed this

Eleventh Day of March, 1997

Attest:

BRUCE LEHMAN

Attesting Officer

Commissioner of Patents and Trademarks